(12) United States Patent
Weil

(10) Patent No.: US 8,243,877 B2
(45) Date of Patent: Aug. 14, 2012

(54) DUAL-USE RADIATION SYSTEM

(76) Inventor: Michael D. Weil, Fort Collins, CO (US)

(*) Notice: Subject to any disclaimer, the term of this patent is extended or adjusted under 35 U.S.C. 154(b) by 105 days.

(21) Appl. No.: 11/853,999

(22) Filed: Sep. 12, 2007

(65) Prior Publication Data

US 2008/0063142 A1 Mar. 13, 2008

Related U.S. Application Data

(60) Provisional application No. 60/825,289, filed on Sep. 12, 2006.

(51) Int. Cl.
*A61N 5/10* (2006.01)
(52) U.S. Cl. .......................... 378/65; 600/427
(58) Field of Classification Search ............. 378/65, 378/151, 152; 600/427
See application file for complete search history.

(56) References Cited

U.S. PATENT DOCUMENTS

| | | | |
|---|---|---|---|
| 4,998,268 A * | 3/1991 | Winter | 378/63 |
| 5,008,907 A | 4/1991 | Norman et al. | |
| 5,555,283 A * | 9/1996 | Shiu et al. | 378/151 |
| 5,661,773 A * | 8/1997 | Swerdloff et al. | 378/65 |
| 5,751,781 A * | 5/1998 | Brown et al. | 378/65 |
| 6,125,295 A * | 9/2000 | Cash et al. | 600/431 |
| 6,207,133 B1 | 3/2001 | Reszka et al. | |
| 6,366,801 B1 | 4/2002 | Cash et al. | |
| 6,463,122 B1 * | 10/2002 | Moore | 378/65 |
| 6,618,467 B1 | 9/2003 | Ruchala et al. | |
| 6,645,464 B1 | 11/2003 | Hainfeld | |
| 6,842,502 B2 * | 1/2005 | Jaffray et al. | 378/65 |
| 6,853,704 B2 * | 2/2005 | Collins et al. | 378/65 |
| 6,865,254 B2 * | 3/2005 | Nafstadius | 378/65 |
| 6,955,639 B2 | 10/2005 | Hainfeld et al. | |
| 7,106,831 B2 * | 9/2006 | Li | 378/152 |
| 7,394,889 B2 * | 7/2008 | Partain et al. | 378/37 |
| 7,486,984 B2 * | 2/2009 | Carroll | 600/436 |
| 2006/0039533 A1 * | 2/2006 | Weil et al. | 378/65 |

OTHER PUBLICATIONS

U.S. Appl. No. 11/671,222, filed Feb. 2007, Weil et al.
U.S. Appl. No. 11/758,001, filed Jun. 2007, Weil.

* cited by examiner

*Primary Examiner* — Allen C. Ho

(57) ABSTRACT

The present invention relates to the field of medical imaging and therapy of lesions that are detrimental to the body. The system is capable of both imaging and treatment with the same kilovoltage radiation source. Dual-use collimators produce a wide beam, which is not a pencil beam or a fan beam, to image and treat a target that has an enhanced radiation cross-section after taking up contrast agent containing a high-Z element. This results in increased radiation dose in the lesion. Furthermore, the significant drop in intensity of a low-energy radiation beam traveling through tissue is surmounted by continually aiming the beam at the target while moving it around the patient. Wide detectors opposing the radiation source permit the imaging and measurement of contrast in the target. More specifically this invention relates to a system, which optimizes delivery of kilovoltage x-rays to a lesion containing contrast agents in higher concentration than the surrounding normal tissues. Thereby subsequent delivery of radiation becomes cytotoxic upon interaction with the contrast.

9 Claims, 4 Drawing Sheets

DUAL-USE RADIATION SYSTEM

RELATED U.S. APPLICATION DATA

This application claims priority of provisional application No. 60/825,289 filed Sep. 12, 2006 and entitled, Dual-Use Radiation System.

REFERENCES CITED

U.S. Patent Documents

| | | |
|---|---|---|
| 5,008,907 | April 1991 | Norman et al. |
| 6,125,295 | September 2000 | Cash and Weil |
| 6,207,133 | March 2001 | Reszka et al. |
| 6,366,801 | April 2002 | Cash and Weil |
| 6,618,467 | September 2003 | Ruchala et al. |
| 6,645,464 | November 2003 | Hainfeld |
| 6,955,639 | October 2005 | Hainfeld and Slatkin |
| SN 11/671,222 | February 2007 | Weil et al. |
| SN 11/758,001 | June 2007 | Weil |

Other Publications

Iwamoto et al., "The CT scanner as a therapy machine," Radiother. Oncol. 19:337, 1990, Elsevier.

Solberg et al., "Calculation of radiation dose enhancement factors for dose enhancement therapy of brain tumours," Phys. Med. Biol. 37:439, 1992, Inst. Phys. Pub.

Iwamoto et al., "Diagnosis and treatment of spontaneous canine brain tumors with a CT scanner," Radiother. Oncol. 26:76, 1993, Elsevier.

Norman et al., "X-Ray phototherapy for canine brain masses," Radiat. Oncol. Investig. 5:8, 1997, John Wiley and Sons.

Mesa et al., "Dose distributions using kilovoltage x-rays and dose enhancement from iodine contrast agents," Phys. Med. Biol. 44:1955, 1999, Inst. Phys. Pub.

Rose et al., "First radiotherapy of human metastatic brain tumors delivered by a computerized tomography scanner (CTRx)," Int. J. Radiat. Oncol. Biol. Phys. 45:1127, 1999, Elsevier.

Weil et al., "Phase I Study of Contrast-Enhanced Radiotherapy with GMCSF for Advanced Cancers," Submitted, 2007.

FIELD OF THE INVENTION

The claimed invention relates generally to medical imaging and therapy of lesions that are detrimental to the body using low-energy radiation with a radiation dose-enhancing agent. The system is capable of both imaging and treatment with the same kilovoltage radiation source and radiation agents.

BACKGROUND OF THE INVENTION

Contrast agents are widely used to improve x-ray or magnetic imaging of soft tissues. Compared to tissue, the heavy elements in diagnostic contrast media have greater capacity to absorb low-energy x-rays. This advantage is described as a higher x-ray "cross section", and is measured by the substance's attenuation coefficient. The preferential blocking of x-rays by a heavy element allows an area to stand out against the background for better imaging, yet also results in more radiation dose delivered to the region nearby. This enhancement of absorbed dose from the contrast media used in radiographic imaging has been viewed as potentially dangerous. Concerns about increased cell damage caused by high radiation doses coming off contrast agents led to the idea that the potentially harmful effects could be exploited to improve radiotherapy Contrast-enhanced radiotherapy (CERT) utilizes previously neglected effects of x-rays absorbed by radiographic contrast agents (U.S. Pat Nos. 6,125,295 and 6,366,801 and U.S. application Ser. No. 11/671,222). Resulting secondary ionizing radiation transfers significant energy and damages a limited volume. After concentrating contrast in a lesion, a lethal radiation dose can be delivered quickly to a lesion with minimal toxicity to nearby tissue. Our previous clinical development of CERT demonstrated the technique could safely create tumor debris in situ. A phase I trial of the technique in advanced cancer patients demonstrated the ability to precisely deliver high doses of x-rays to tumors with no toxicity and good palliation (Weil et al., "Phase I Study of Contrast-Enhanced Radiotherapy with GMCSF for Advanced Cancers," Submitted, 2007).

The most important interactions between 120-150 kVp x-rays and a contrast agent are the attenuation (measured as, $\mu_{en}$, mass attenuation coefficient) and energy transfer (measured as, $\mu_{en/p}$, mass energy-absorption coefficient) as a result of collisions with the electrons in a high Z element, such as iodine. Iodine is commonly used for imaging since it is the high Z element in commercially available CT contrast media The image reconstruction algorithm of a CT scanner employs numbers, Hounsfield units (HU), which are calculated as the beam spectrum is attenuated by the tissue in the patient, $$HU = 1000(\mu_{tissue} - \mu_{water})/\mu_{water} \quad \text{(Eqn. 1)};$$

where, $\mu_{tissue}$ and $\mu_{water}$ are the linear attenuation coefficients for tissue and water, respectively. Thus, the CT numbers (HU) have a linear relationship with the x-ray attenuation coefficients, and a Hounsfield Unit represents a change of 0.1% in the attenuation coefficient of water.

Marketed CT software readily acquires HU of injected pixels directly from the image. From the measured HU, the known mass attenuation coefficients from the National Institute of Standards and Technology for a given beam energy can be used to derive the concentration of iodine. In the above equation, $\mu_{tissue}$ is replaced by, $$\mu_{iodine} \times [\text{iodine concentration}].$$

On the other hand, the accompanying increase in energy transfer can enhance the dose delivered to a lesion by more than an order of magnitude. The dose enhancement factor (DEF) can be calculated for iodine versus water at a given energy as:

$$DEF = \frac{(\mu_{en/\rho})_1 * f_1 + [(\mu_{en/\rho})_{H2O} * (1 - f_1)]}{(\mu_{en/\rho})_{H2O}}; \quad \text{(Eqn. 2)}$$

where $\mu_{en/p}$ is the mass energy-absorption coefficient of iodine or water (at the spectral energy), and $f_1$ is the fraction by weight of iodine in the lesion.

The DEF can be as high as 37:1 with commercially available iodinated-CT contrast media, which was sufficient to destroy most tumors in our study. Moreover, the delineation between the high dose in the contrast-painted tumor to the low dose in the tissue takes place in under 50 μm(<$10^{-4}$ m).

Comparable fall-off for all other therapeutic radiation techniques, e.g., megavoltage beams, seeds, particles, is on the order of centimeters ($10^{-2}$ m).

An infused lesion is imaged and the concentration of high Z material in the target is determined. If the imaging is done with a CT scanner the CT numbers (Hounsfield Units) can be used to calculate the dose enhancement factor for CERT. Likewise, if a different type of digital detector is employed the dose enhancement factor can be derived from the attenuation coefficients measured with multiple beams. If, after calculating the dose enhancement factor for CERT, the potential enhancement is too low, the contrast infusion is repeated until there is sufficient high Z material in the target to produce adequate dose enhancement. Following delivery of radiation agents and confirmation of a minimal contrast concentration; the lesion is treated with radiation. The radiation is best delivered with external radiation beams from multiple directions. It is extremely difficult to deliver radiotherapy beams from multiple directions with existing kilovoltage technology.

Another critical component of this invention is quantification and dosimetry of the delivered dose of radiation. The penetration of the radiation through tissue will decrease the flux and also change the spectrum by hardening the beam, i.e., the average beam energy increases as lower energy photons are attenuated and higher energy photons relatively predominate. These parameters are influenced by the residence time of the radiation agent in the tumor and are dependent upon the kinetics of diffusion out of the target site. In clinical practice these variables are accounted for and the DEF is calculated with planning software.

This invention does not employ radiopharmaceuticals. The high doses to the organs when using radioactive targeting moieties limit the use of the technology. The utility of the radiation treatment agents with dual-use collimation of kilovoltage radiation described herein, especially absent attached radioactive isotopes, for enhancing the effect of radiation therapy has not been taught elsewhere.

The types of tumors that can be treated by this invention include primary and metastatic bone and soft tissue tumors. When the location of these tumors is known, one modality of treatment is to administer the radiation agent, then concentrate the radiation to the area of the tumor, thus increasing the ratio of absorbed radiation dose in the target versus normal tissue. In other cases, where many tumors are in need of treatment, or where there is disseminated disease, it is possible to administer the radiation agent then give relatively low radiation to the whole body. This way of treating the patient may treat micro-metastatic sites, or small tumors, before they grow into bigger and less treatable tumors.

Contrast agents and tumor targeting techniques at present do not achieve adequate tumor concentration of heavy atoms for CERT except with direct intratumoral injection of contrast (U.S. Pat. Nos. 6,125,295 and 6,366,801 and Weil et al., "Phase I Study of Contrast-Enhanced Radiotherapy with GMCSF for Advanced Cancers," Submitted, 2007). In the example from Hainfeld et al (U.S. Pat. Nos. 6,645,464 and 6,955,639) employing intravenous delivery of gold nanoparticles into experimental mouse tumors; they measured gold uptake in the tumor at 0.23% weight/volume. However, for practical implementation of CERT, it is necessary to obtain ~2.5-30% weight/volume of a heavy element in a tumor. Therefore, as reported in this study with gold nanoparticles, the dose enhancement would be 10-100 times less than required for clinical efficacy.

The prospects of safely using kilovoltage beams even for tumors at depth are improved with a significant DEF. Rather than overdosing the skin in an effort to increase the radiation dose to a deep lesion, the DEF may enable treatment with lethal dosing of the tumor and relatively low dose to the skin. However, as a result of significant tissue absorption of kilovoltage x-rays, tumors deeper than 5 cm require multiple beams in order to safely deliver an adequate radiation dose.

Others have employed devices to use a single machine for imaging and therapy. Norman et al have described treatments employing a kilovoltage computerized tomography scanner with collimation altered to produce a pencil beam, a small round or rectangular beam (U.S. Pat. No. 5,008,907; Iwamoto et al., "The CT scanner as a therapy machine," Radiother. Oncol. 19:337, 1990, Elsevier; Solberg et al., "Calculation of radiation dose enhancement factors for dose enhancement therapy of brain tumours," Phys. Med. Biol. 37:439, 1992, Inst, Phys. Pub.; Iwamoto et al., "Diagnosis and treatment of spontaneous canine brain tumors with a CT scanner," Radiother. Oncol. 26:76, 1993, Elsevier; Norman et al., "X-Ray phototherapy for canine brain masses," Radiat. Oncol. Investig. 5:8, 1997, John Wiley and Sons.; Mesa et al., "Dose distributions using kilovoltage x-rays and dose enhancement from iodine contrast agents," Phys. Med. Biol. 44:1955, 1999, Inst. Phys. Pub.; Rose et al., "First radiotherapy of human metastatic brain tumors delivered by a computerized tomography scanner (CTRx)," Int. J. Radiat. Oncol. Biol. Phys. 45:1127, 1999, Elsevier). These treatments were done with fractionated radiotherapy. The use of megavoltage computerized tomography capable of imaging and treatment has also been developed (U.S. Pat. No. 6,618,467).

The therapeutic profile of contrast-enhanced radiotherapy can be of benefit since tumor control rates are better with increased radiation doses. To satisfactorily enhance the kilovoltage radiation dose absorbed by a solid tumor in the presence of a high Z element, it is necessary to be able to safely deliver adequate radiation to all locations in the body. Improved efficacy and/or control of such delivery are desired.

SUMMARY OF THE INVENTION

To address at least the foregoing, some embodiments of the present invention provide a system, apparatus, method and means to generate an image and radiation treatment with a single radiation source modified with dual-purpose collimation, a capability to move in an arc or circle about a patient while aiming at the internal target, and enhance the radiation dose safely in the target loaded with a radiation enhancing agent. In a further aspect, the painted internal target is first imaged and then a radiation treatment plan is determined.

According to some embodiments, a dual-use collimator produces a wide-based pyramidal beam, which continually is aimed at a contrast-enhanced lesion, while the radiation source is tracked around the patient to minimize skin dosing. The treatment parameters for the radiation treatment plan are derived from the reconstructed measurements used to create an image and then the treatment can be delivered safely with high precision in a minimal number of treatment sessions. The radiation dose enhancement results from interactions between kilovoltage x-rays and the high Z element in contrast agents distributed in a tumor. The invention does not require megavoltage radiation or radiation treatment with a pencil beam.

In still further aspects, a radiation source can be mounted in opposition to a digital detector with a C-arm. The apparatus can move about an internal tumor containing a radiation treatment agent and treated to high radiation dose. Alternatively, a CT scanner can be modified with a dual-use collimator to produce a wide-based pyramidal or circular beam and moved around a target for imaging and treatment. A wide detector, or array of detectors, captures the beam for processing. The dose enhancement from the kilovoltage beam's interaction with contrast is calculated and displayed with treatment planning software.

The claimed invention is not limited to the disclosed embodiments, however, as those in the art can readily adapt the description herein to create other embodiments and applications.

BRIEF DESCRIPTION OF THE FIGURES

The construction and usage of embodiments will become readily apparent from consideration of the following specification as illustrated in the accompanying drawings, in which like reference numerals designate like parts, and wherein.

DETAILED DESCRIPTION OF THE INVENTION

Figure 1:
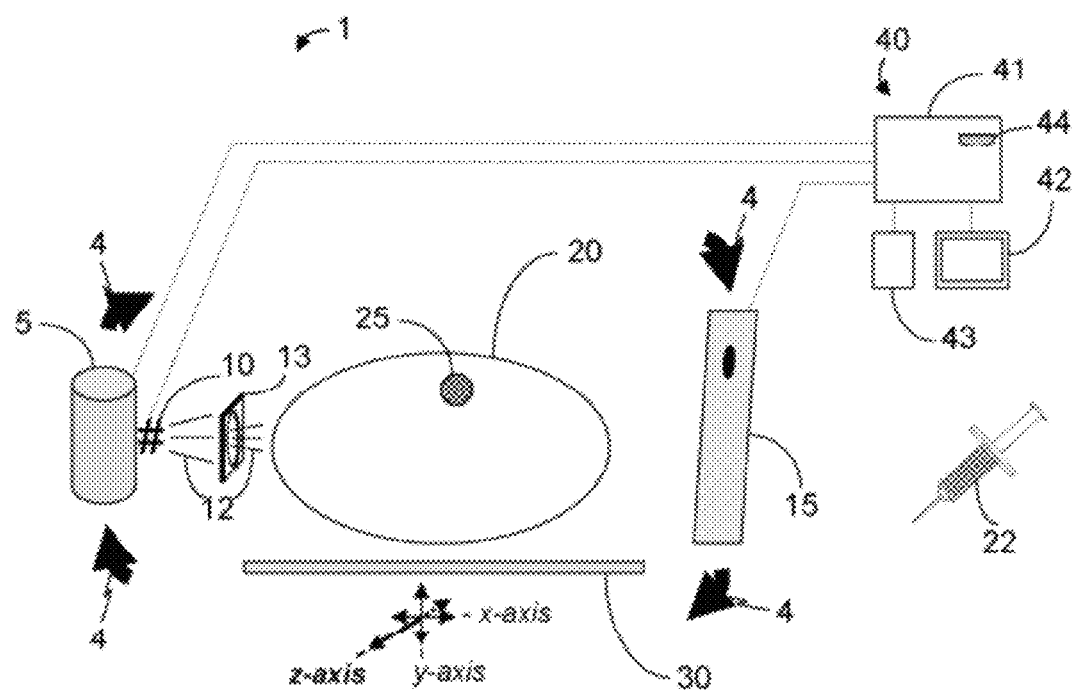
FIG. 1 is a diagram illustrating a system according to some embodiments.

The construction and usage of embodiments will become readily apparent from consideration of the following specification as illustrated in the accompanying drawings, in which like reference numerals designate like parts, and wherein:

FIG. 1 is a diagram illustrating a system according to some embodiments. System 1 comprises dual-use radiation source 5 containing dual-use collimators 10 and detector 15. According to some embodiments, dual-use collimators 10 are usable for creating a diagnostic image and treating an identified lesion according to a radiation treatment plan. As will be described in detail below, the dual-use collimators 10 might be associated with imaging and/or radiation treatment planning software 44.

Radiation source 5 may comprise any currently or hereafter know device that is capable of treating tissue with radiation, e.g., kilovoltage x-rays. The radiation emitted from radiation source 5 is contoured by dual-use collimators 10 that shape the x-rays into a wide pyramidal beam 12, which is neither a fan beam nor a pencil beam. Opposing the beam is digital detector 15, which measures and images the beam 12 after in passes through patient 20 and lesion 25. Radiation source 5 and detector 15 can move about patient 20 but detector 15 is always maintained in a position opposing radiation source 5. The path about the patient 20 and internal lesion 25 is indicated by arrows 4. The patient 20 lies on a movable table 30 for positioning during acquisition of the image and better alignment of the target 25 during treatment. The table 30 can move in three-dimensions, i.e., left and right (x-axis), in addition to up and down (y-axis), and in and out of the plane of the drawing (z-axis), to better situate the target 25 relative to the radiation source 5 for treatment.

The digital detector 15 may comprise an image intensifier and camera, a flat-panel device using a scintillator layer and solid-state amorphous silicon photodiodes deployed in a two-dimensional array, or any detector system used in CT scanners. The digital detector 15 may also convert x-rays to electrical charge and store it without use of a scintillator layer. In such devices, x-rays are absorbed directly by an array of amorphous selenium photoconductors. The photoconductors convert the x-rays directly to stored electrical charge that comprises an acquired image of a radiation field. Digital detector 15 may also comprise a CCD or tube-based camera.

Prior to imaging or treatment with radiation in the kilovoltage energy range, the absorption cross-cross section of the target 25 is enhanced by the administration of a radiation treatment agent 22 containing an element having an atomic weight greater than fifty (U.S. Pat. Nos. 6,125,295 and 6,366,801, and U.S. application Ser. No. 11/758,001). Accordingly, radiation treatment agent 22 may compromise a heavy element-containing compound in some embodiments, e.g., iodine, gold, or bismuth. Since a radiation beam will be more readily stopped by the volume of radiation agent 22 in the target 25, the painted target 25 will be more damaged than the surrounding normal tissue without the heavy element. The radiation treatment agent 22 is not itself radioactive; it reacts to radiation from radiation source 5.

However, despite the increase in radiation dose in a target 25 as a result of the its uptake of radiation agent 22, to deliver sufficient radiation dose to safely destroy a pathological lesion anywhere in the body requires kilovoltage x-ray beams 12 aimed at the target 25 from multiple angles. Therefore, the system 1 must be capable of moving the radiation source 5 and digital detector 15 around the patient 20 while keeping the target 25 in the radiation beam 12.

The operator station 40 of system 1 includes computers 41 in communication with a display 42 and an entry device 43 such as a keyboard. The computer 41 may be a dedicated part of system 1 or may be in communication at a distance. The computer 41 may facilitate diagnostic scanning and contain software medium 44 to reconstruct images from data acquired by detector 15. An operator may employ the operator station 40 to instruct radiation unit 50 to deliver x-ray radiation 12 to the patient 20 for diagnosis or radiation treatment according to a radiation treatment plan in processor 41. Operator station 40 may also or alternatively be used to generate the radiation treatment plan. In this regard, operator station 40 may generate the treatment plan by importing computed tomography images, or other acquired images, and then executing inverse treatment planning based on the images. The treatment plan may then be exported to an application for controlling radiation unit 50.

Operator station 40 may be located apart from radiation unit 50, such as in a different room, in order to protect the operator from radiation. It should be noted, however, that the operation of low-voltage radiation systems does not require protective measures to the extent of those required during megavoltage radiation treatment, often resulting in less costly treatment. The operator station 40 can interface with others elements in the dual-use radiation system 1 in some embodiments including radiation source 5 control, dual-use collimator 10 control, CT gantry 7 control, table 30 control and imaging detector 15 control. Computer processor 41 further includes microprocessor and memory.

Software medium 44 may design and store a radiation treatment plan in computer-readable and executable formats to calculate the therapeutic effects of radiation treatment with multiple beams 12 in the presence of radiation agent 22. Such software medium 44, for a spectrum of beam energies from a particular radiation source 5 will model the dissipation of beam flux 12 by tissue absorption and the dose enhancement due to the interaction with radiation agent 22. The calculation of radiation dose enhancement in an internal target 25 containing radiation agent 22 following treatment with the beam 12 shaped by dual-use collimator 10 is unique for radiation treatment planning. Other radiation treatment planning accounts for the dose reduction as radiation travels in tissue.

System 1 may include less or more elements than depicted in FIG. 1. Non-exhaustive examples of such elements include fixed wide collimators, intensity modulation of radiation sources, or other radiation sources. System 1 may also be configured in suitable fashions other than that shown in FIG. 1.

The elements of system 1 may be associated within a single package by any one or more entities. A manufacturer or reseller of radiation source 5, dual-use collimators 10, digital detector 15, software medium 44, or treatment table 30 may create system 1 and provide system 1 to entities that deliver radiation treatment. In addition, a manufacturer or reseller may also produce system 1 to work with a particular radiation agent 22.

Figure 2:
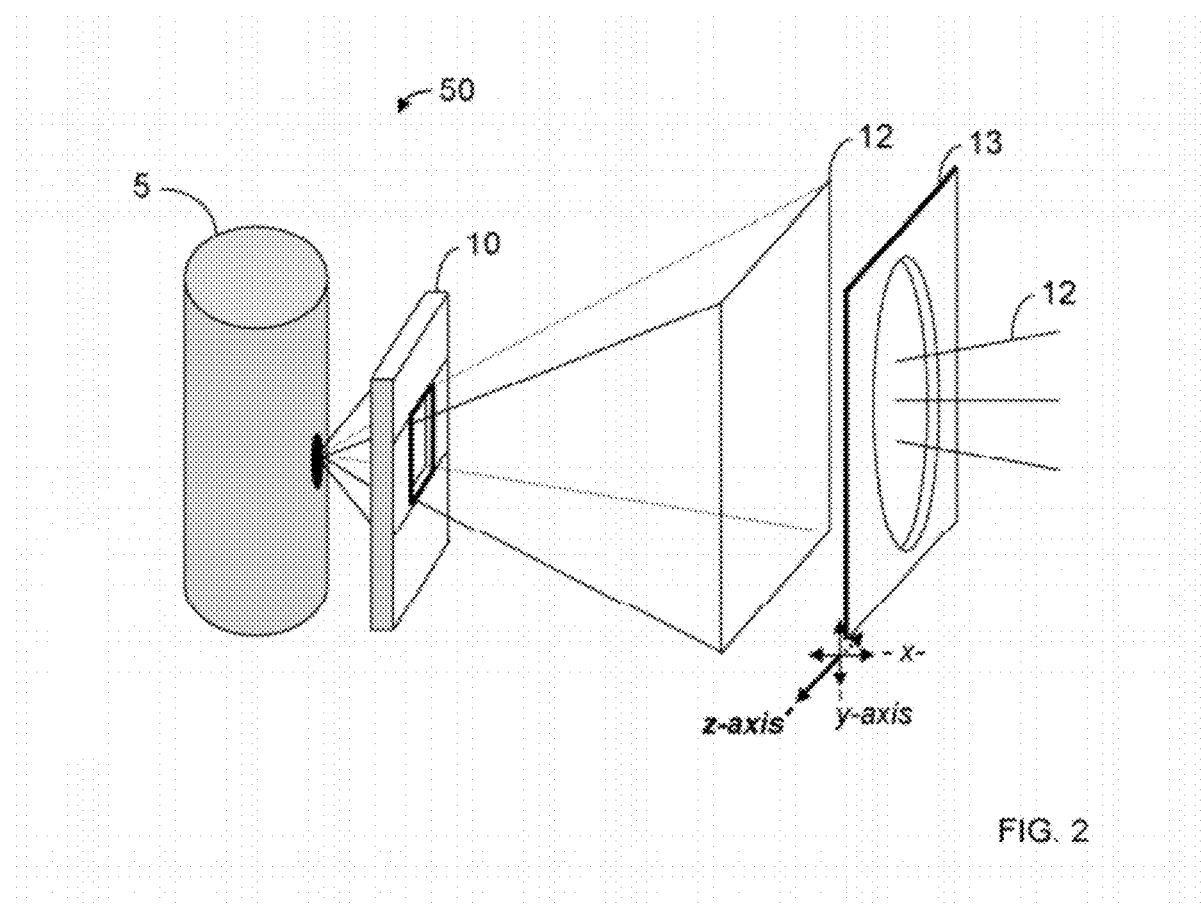
FIG. 2 is a simplified perspective view of dual-use radiation delivery components according to some embodiments.

FIG. 2 is a simplified perspective view of dual-use radiation delivery components 50 according to some embodiments. Dual-use radiation delivery components 50 comprise radiation source 5 and dual-use collimators 10. According to some embodiment, delivery system 1 is used to deliver radiation to patient 20 according to a radiation treatment plan. The radiation source 5 is a beam-emitting device, such as an x-ray tube for delivering radiation. The radiation may have energies ranging from 18 to 300 keV. The radiation emitted by radiation source 5 may comprise any radiation suitable for data acquisition, imaging and/or treatment according to some embodiments. In some embodiments, the radiation is suitable to produce dose-enhancing effects when used in conjunction with a radiation treatment agent 22 that is capable of treating tissue 25 following received radiation. In general, the x-ray tubes presently in use for imaging have small anodes, which make cooling for a therapeutic load more difficult. However, newer CT tubes have much improved power and cooling capabilities. The radiation source 5 does not produce megavoltage radiation as claimed under U.S. Pat. No. 6,618,467.

Radiation source 5 may also include beam-shaping devices such as one or more jaws, collimators, reticles and apertures, including dual-use collimators 10. In one such embodiment in FIG. 2, dual-use collimators 10 contour the beam for diagnosis and/or treatment along the z-axis (the long axis of treatment table 30) and either the y-axis (ceiling-floor) or the x-axis (left-right) thus producing a wide-base pyramidal beam 12. Compared to conventional CT collimation the field is significantly greater in the direction of the z-axis (the long axis of treatment table 30) and significantly smaller in either the direction of the y-axis (ceiling-floor) or the x-axis (left-right). In the example given, the shaped beam produces a rectangular field, but in other embodiments the field geometry could be circular, ovoid or polygonal by using secondary blocking 13 with multi-leaf collimation or conical shaping forms. The size and shape of the beam are adjustable, but the size of the beam field at the internal target 25 is 10 mm by 10 mm or greater. The greater field size in the z-axis is critical to rapidly treat lesions greater than 1 cm in that direction. The smaller field size in the y- or x-axis is critical to minimizing the skin dose when treating from multiple directions. Additional optimization of radiation source 5 and dual-use collimators 10 beam output can be achieved by intensity modulation of radiation source 5 current flow and dynamic changes in dual-use collimator 10 position with varying treatment beam 12 positions. The dual-use collimators 10 do not produce a pencil beam as claimed under U.S. Pat. No. 5,008,907. Furthermore, the wider radiation field does not require the internal target 25 to be aligned at the isocenter of an arcing beam.

Figure 3:
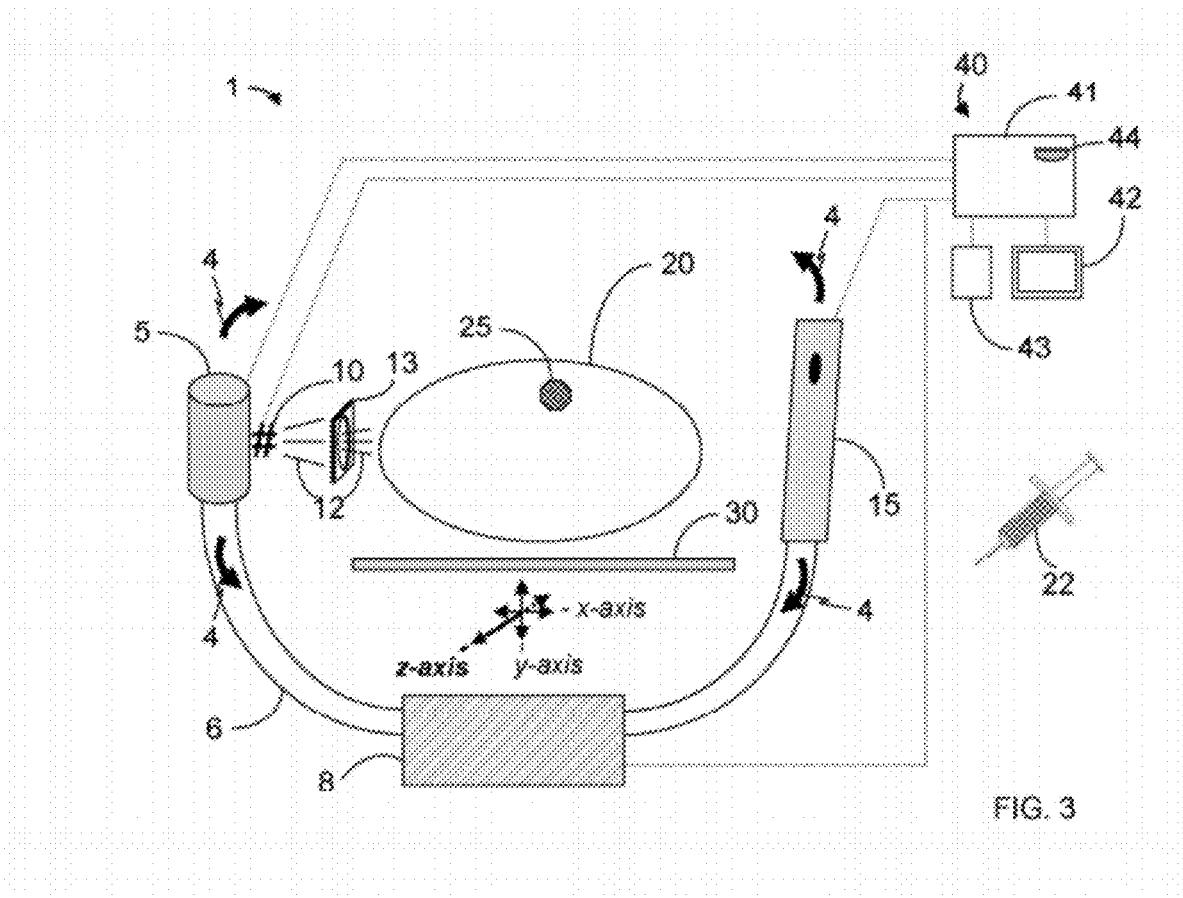
FIG. 3 is a diagram illustrating elements of a dual-use radiation system according to some embodiments.

FIG. 3 is a diagram illustrating elements of a dual-use radiation system according to some embodiments. Radiation source 5 and digital detector 15 may be coupled to C-arm 6 so as to face one another irrespective of any movement of the C-arm 6 with respect to its base 8 as shown in FIG. 3. In this regard, C-arm 6 is slidably mounted on base 8 and can therefore be moved in order to change the position of radiation source 5 with respect to treatment table 30. Treatment table 30 may also be adjustable to assist in positioning an internal portion 25 of the patient 20 with respect to the radiation unit 50. In some embodiments, base 8 includes a high-voltage generator for supplying power used by radiation source 5 to generate kilovoltage radiation.

Many C-arm/base configurations may be used in conjunction with some embodiments, including portable configurations, wall or ceiling mounted, or robot mounted configurations. In some embodiments, radiation source 5 with dual-use collimator 10 and digital detector 15 are mounted on robot arms with coordinated movement about patient 20 and internal target 25.

Figure 4:
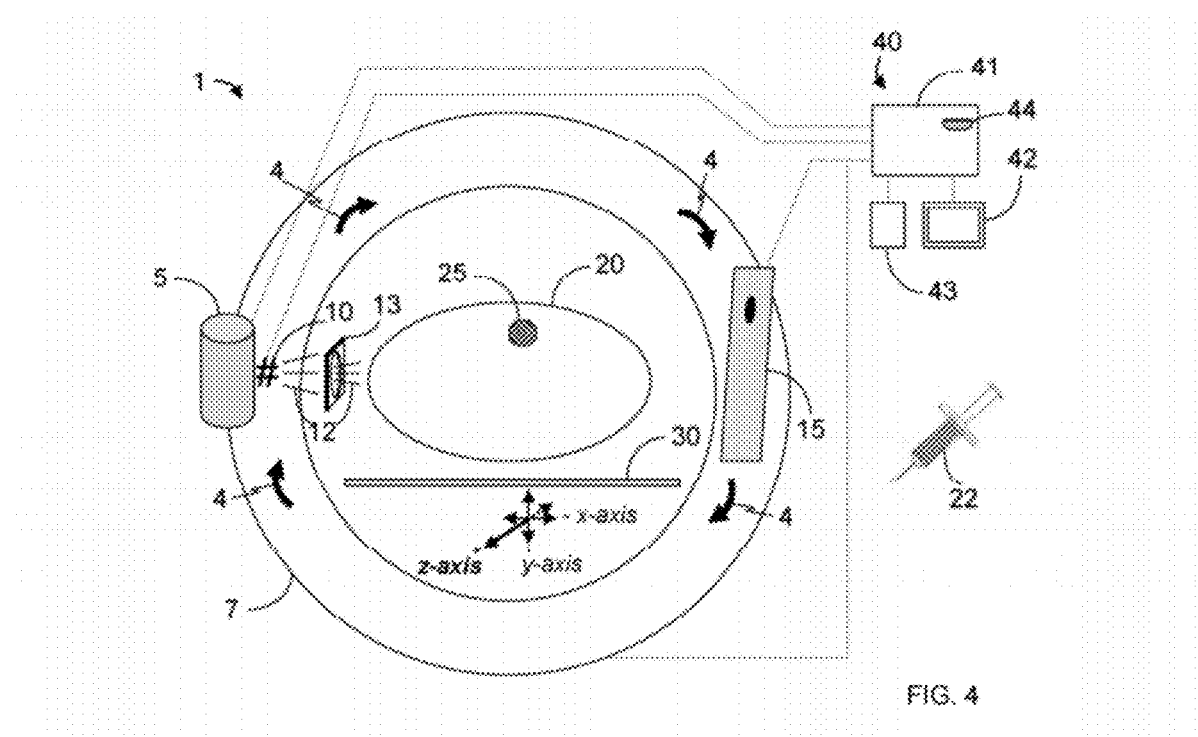
FIG. 4 is a diagram illustrating elements of a dual-use radiation system according to some embodiments.

FIG. 4 is a diagram illustrating elements of a dual-use radiation system according to some embodiments. Radiation source 5 with dual-use collimator 10 and digital detector 15 may be coupled in CT scanner 7 so as to face one another irrespective of any movement of CT scanner 7 with respect to the patient 20 and an internal target 25 as shown in FIG. 4. In such embodiments, the dual-use collimator 10 replaces conventional diagnostic CT collimation to safely permit diagnostic scanning and therapy. In some embodiments, detector 15 is of adequate size in the z-axis to encompass the larger radiation beam 12. Diagnostic imaging and radiation treatment are performed by movement of the radiation source 5 with dual-use collimator 10 about the patient 20 and internal target 25. Images are reconstructed from data gathered by detector 15 with CT software medium 44. Treatment is performed according to radiation planning software 44 using images of the patient 20 to target a lesion 25 containing radiation agent 22. The treatment table 30 may also be adjustable in the x-axis in addition to the other dimensions to assist in positioning an internal portion 25 of the patient 20 with respect to the radiation unit 50 according to the radiation treatment plan. In some embodiments, CT scanner 7 includes a high-voltage generator for supplying power used by radiation source 5 to generate kilovoltage radiation.

What is claimed is:

1. A system comprising:
   a single movable kilovoltage x-ray radiation source emitting a kilovoltage x-ray beam;
   a dual-use collimator to contour the kiloyoltage x-ray beam to produce a wide-based pyramidal kilovoltage x-ray beam for imaging and treating pathologic lesions according to a radiation treatment plan;
   a treatment table having a long axis with movement in three dimensions;
   a wide digital radiation detector or array of detectors opposite the radiation source of adequate size in a z-axis (the long axis of the treatment table) to capture the wide-based pyramidal kilovoltage-x-ray beam for processing wherein the wide-based pyramidal kilovoltage x-ray beam is measured and imaged after it passes through a patient and the lesions;
   an injector device that supplies a quantity of a radiation treatment agent to a patient;
   an, operator station including computers and software medium to facilitate diagnostic scanning and to reconstruct images from data acquired by the wide detector capturing the wide-based pyramidal kilovoltage x-ray beam;
   wherein the medium stores computer-executable process steps to reconstruct medical images from data acquired by the wide detector and calculate a plan with therapeutic effects of a wide-based pyramidal kilovoltage x-ray beam radiation treatment.

2. A system according to claim 1, wherein:
the kilovoltage x-ray beam has energies ranging from 18 to 300 keV;
the dual-use collimator contours the kilovoltage x-ray beam along the z-axis (the long axis of the treatment table) and either the y-axis (ceiling-floor) or the x-axis (left-right) thereby producing the wide-based pyramidal kilovoltage x-ray beam;
wherein a contoured wide-based pyramidal kilovoltage x-ray field is significantly greater in the direction of the z-axis (the long axis of the treatment table) and significantly smaller in either the direction of the y-axis (ceiling-floor) or the x-axis (left-right) compared to a fan beam;
the wide-based pyramidal Isilovoltage x-ray beam is acquired and reconstructed into an image and treats pathologic tissue with an enhanced radiation cross-section after taking up contrast agent containing a high-Z element;
wherein the greater field size in the z-axis permits rapid treatment of fields greater than 1 cm in that direction and does not require precise alignment of an isocenter of an arcing beam.

3. A system according to claim 2, further comprising:
secondary blocking to contour different shapes and sizes of the wide pyramidal beam;
wherein the secondary blocking comprises a multileaf collimator configured to adjust a field geometry of the wide pyramidal beam;
wherein a radiation field size at an internal target is greater than 10 mm by 10 mm; and
a medium, which stores computer-executable process steps to adjust the mechanism's position for imaging and treatment using wide-based kilovoltage x-ray beams according to radiation planning in the presence of the high-Z element.

4. A system according to claim 1 wherein:
the radiation treatment agent is a kilovoltage x-ray radiation dose-enhancing agent;
radiation interacting with the radiation treatment agent is the wide-based kilovoltage x-ray beam.

5. A system comprising:
a CT scanner with a kilovoltage x-ray radiation source that produces a kilovoltage x-ray beam;
wherein the CT scanner has a dual-use collimator to shape the kilovoltage x-ray beam into a wide-based pyramidal kilovoltage x-ray beam for imaging and treating pathologic lesions according to a radiation treatment plan;
wherein the CT scanner has a treatment table having a long axis with movement in three dimensions;
a wide digital radiation detector or array of detectors opposite the radiation source of (adequate size in a z-axis (the long axis of the:treatment table) to capture the wide-based pyramidal kilovoltage,x-ray beam for processing wherein the wide-based pyramidal kilovoltage x-ray beam is measured and imaged after it passes through a patient and the lesions;
an injector device that suppliesa quantity of a radiation treatment agent to a patient;
an operator station including computers and software medium to facilitate diagnostic scanning and to reconstruct images from data acquired by the wide detect& captunng the wide-based pyramidal kilovoltage x-ray beam;
wherein the medium stores compUter-exacutable process steps to reconstruct-medical images from data acquired by the wide detector and calculate a plan with therapeutic effects of a wide-based pyramidal kilovoltage x-ray beam radiation treatment.

6. A system according to claim 5 wherein:
the kilovoltage radiation beam has energies ranging from 18 to 300 keV;
the dual-use collimator shapes the kilovoltage radiation beam emitted from the source into a wide pyramidal beam;
the dual-use collimator contours the kilovoltage x-ray beam along the z-axis (the long axis of the treatment table) and either the y-axis (ceiling-floor) or the x-axis (left-right) thereby producing a wide-based pyramidal kilovoltage x-ray beam;
wherein a contoured wide-based pyramidal kilovoltage x-ray field is significantly greater in the direction of the z-axis (the long axis of the treatment table) and significantly smaller in either the direction of the y-axis (ceiling-floor) or the x-axis (left-right) compared to a fan beam;
the wide-based pyramidal kilovoltage x-ray beam is acquired and reconstructed into an image and treats pathologic tissue with an enhanced radiation cross-section after taking up contrast agent containing a high-Z element;
wherein the greater field size in the z-axis permits rapid treatment of fields greater than 1 cm in that direction and does not require precise alignment of an isocenter of an arcing beam.

7. A system according to claim 6 further comprising:
secondary blocking to contour different shapes and sizes of the wide pyramidal beam;
wherein the secondary blocking comprises a multileaf collimator configured to adjust a field geometry of the wide pyramidal beam;
wherein a radiation field size at an internal target is greater than 10 mm by 10 mm; and
a medium, which stores computer-executable process steps adjusts the mechanism's position for imaging and treatment using wide-based kilovoltage x-ray beams according to radiation planning in the presence of the high-Z element.

8. A method comprising:
capturing a wide-based pyramidal kilovoltage x-ray beam by a wide digital radiation'detector or array of detectors to acquire data, wherein the wide digital radiation detector or array of detectors is of adequate size in a z-axis (the lonq axis of a treatment table):
processing the data to generate an x-ray radiation treatment plan associated with a radiation treatment agent interacting with the wide-based pyramidal kilovoltage x-ray beam; and
treating a lesion with moving external wide-based pyramidal kilovoltage x-ray radiation beams.

9. A method according to claim 8, further comprising:
employing the radiation treatment agent for lesions in the head or body wherein the lesions are primary or metastatic cancers, or non-cancerous lesions, vascular plaques, or nervous system lesions; and
administering the radiation treatment agent then giving low radiation dose to the whole body.

* * * * *